(12) United States Patent
Thompson

(10) Patent No.: US 7,027,861 B2
(45) Date of Patent: Apr. 11, 2006

(54) METHOD AND APPARATUS FOR AFFECTING ATRIAL DEFIBRILLATION WITH BI-ATRIAL PACING

(75) Inventor: David L. Thompson, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 423 days.

(21) Appl. No.: 09/974,079

(22) Filed: Oct. 9, 2001

(65) Prior Publication Data

US 2003/0069609 A1   Apr. 10, 2003

(51) Int. Cl.
*A61N 1/362*   (2006.01)

(52) U.S. Cl. .............................. 607/4; 607/14

(58) Field of Classification Search ............... 607/4, 607/9, 14, 17, 25–26; 600/509, 516, 517
See application file for complete search history.

(56) References Cited

U.S. PATENT DOCUMENTS

| | | | |
|---|---|---|---|
| RE27,652 E | 5/1973 | Mirowski et al. | 128/419 |
| 3,738,370 A | 6/1973 | Charms | 128/419 |
| 3,942,536 A | 3/1976 | Mirowski et al. | 128/419 |
| 3,952,750 A | 4/1976 | Mirowski et al. | 128/419 |
| 4,161,952 A | 7/1979 | Kinney et al. | 128/786 |
| 4,481,953 A | 11/1984 | Gold et al. | 128/786 |
| 4,577,633 A | 3/1986 | Berkovits et al. | 128/419 |
| 4,587,970 A | 5/1986 | Holley et al. | 128/419 |
| 4,708,145 A | 11/1987 | Tacker, Jr. et al. | 128/419 |
| 4,726,380 A | 2/1988 | Vollmann et al. | 128/419 |
| 4,727,877 A | 3/1988 | Kallok | 128/419 |
| 4,830,006 A | 5/1989 | Haluska et al. | 128/419 |
| 4,880,005 A | 11/1989 | Pless et al. | 128/419 |
| 5,014,696 A | 5/1991 | Mehra | 128/419 |
| 5,042,143 A | 8/1991 | Holleman et al. | 29/825 |
| 5,117,824 A | 6/1992 | Keimel et al. | 128/419 |
| 5,165,403 A | 11/1992 | Mehra | 128/419 |
| 5,269,298 A | 12/1993 | Adams et al. | 128/419 |
| 5,331,966 A | 7/1994 | Bennett et al. | 128/696 |
| 5,433,729 A | 7/1995 | Adams et al. | 607/5 |
| 5,514,161 A | 5/1996 | Limousin | 607/9 |
| 5,645,569 A * | 7/1997 | Ayers | 607/4 |

(Continued)

FOREIGN PATENT DOCUMENTS

EP   1062987   * 12/2000

OTHER PUBLICATIONS

Blanc et al, Safety and Feasibility of Transvenous Cardioversion in Atrial Tachycardia, Cardiac Pacing, 1985, pp 1526-1530.

(Continued)

*Primary Examiner*—Robert E. Pezzuto
*Assistant Examiner*—Kristen Mullen
(74) *Attorney, Agent, or Firm*—Michael C. Soldner; Girma Wolde-Michael

(57) ABSTRACT

A method and apparatus for cardioverting the atrium of a human heart that includes insertion of first and second elongated electrodes tranvenously into the heart and associated vessels. One electrode is preferably located in the coronary sinus and great vein of the heart. The other electrode is preferably located in the vicinity of the right atrium of the heart, spaced from the electrode located in the coronary sinus. In response to detection of fibrillation or in response to manual triggering, a defibrillation pulse is applied between the first and second electrodes to effect atrial cardioversion. Further, after delivery of a successful defibrillation shock, the width of intrinsic p-waves are monitored and bi-atrial pacing is temporarily initiated if the width exceeds a preset or programmable threshold.

35 Claims, 5 Drawing Sheets

U.S. PATENT DOCUMENTS

| | | | | |
|---|---|---|---|---|
| 5,676,687 | A | * | 10/1997 | Ayers ............................ 607/4 |
| 5,902,324 | A | | 5/1999 | Thompson et al. ............ 607/9 |
| 6,029,087 | A | | 2/2000 | Wohlgemuth ................... 607/9 |
| 6,070,101 | A | | 5/2000 | Struble et al. ................. 607/9 |
| 6,122,545 | A | | 9/2000 | Struble et al. ................. 607/9 |
| 6,292,694 | B1 | * | 9/2001 | Schloss et al. ................. 607/9 |
| 6,505,067 | B1 | * | 1/2003 | Lee et al. .................... 600/509 |
| 2003/0060850 | A1 | * | 3/2003 | Zhu ............................... 607/9 |

OTHER PUBLICATIONS

H. F. Tsc et al, Recurrence of Atrial Fibrillation After Successful Cardioversion with Transvenous Atrial Defibrillation is Associated with Prolonged P Wave, European Journal of Cardiac Pacing and Electrophysiology, Jun. 1996, vol. 6, No. 1, p 55, 218 22/PW8.

Theres et al, Electrogram Signals Recorded from Acute and Chronic Pacemaker Implantation Sites in Pacemaker Patients, Jan. 1998, PACE, vol. 21, p. 11.

Arzbaecher et al, Automatic Tachycardia Recognition, PACE, May-Jun. 1984, vol. 7, p 541-547.

S. C Jain et al, Elective Countershock in Atrial Fibrillation with an Intracardiac Electrode—A Preliminary Report, Paper Read at Joint Session of the Association of Physicians of India and Cardiology Society of India—Bombay—Jan. 1970.

* cited by examiner

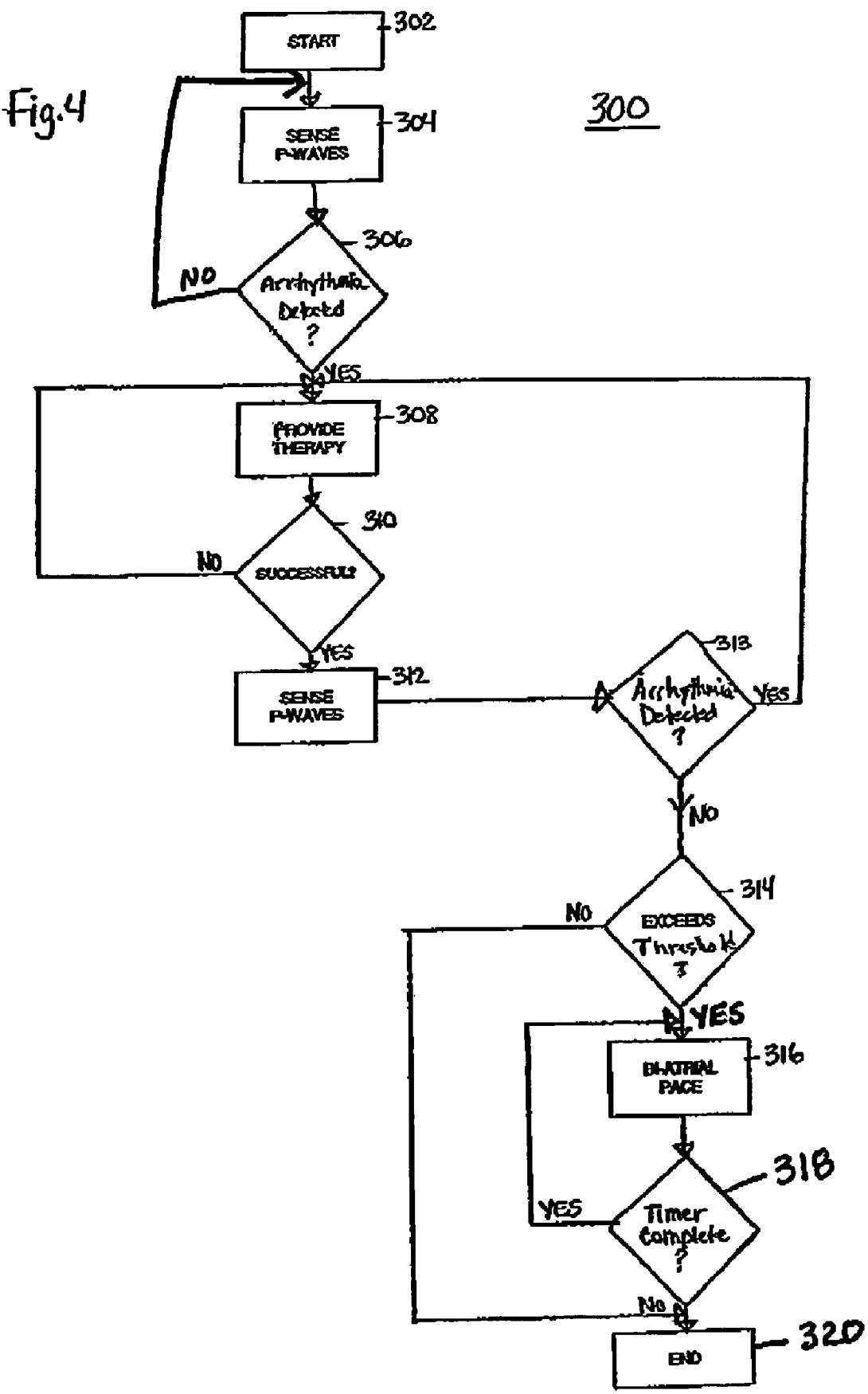

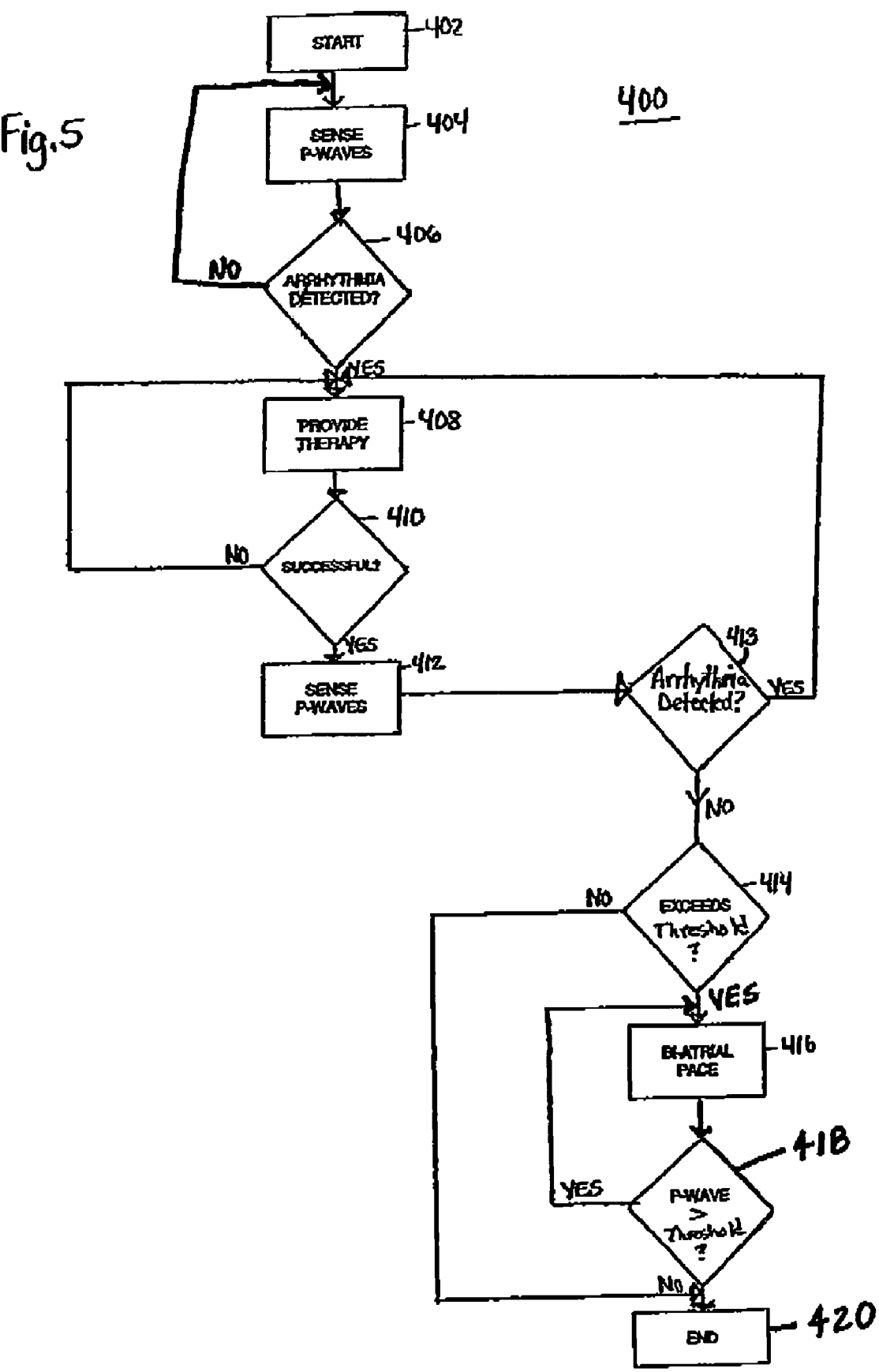

METHOD AND APPARATUS FOR AFFECTING ATRIAL DEFIBRILLATION WITH BI-ATRIAL PACING

BACKGROUND OF THE INVENTION

The present invention relates to implantable cardioverters/defibrillators generally, and more particularly to an implantable bi-atrial pacemaker/defibrillator with capability of atrial fibrillation reoccurrence prevention.

Early concepts of implantable defibrillators, such as those disclosed in Reissue Pat. No. 27,652 by Mirowski, et al, envision an electrode system employing a ventricular endocardial electrode and a plate electrode mounted to the heart directly, subcutaneously, or to the skin. However, it has long been recognized that a totally transvenous system would be desirable in order to simply the use of implantable defibrillators. One such system is suggested in Mirowski, et al U.S. Pat. No. 3,942,536, which discloses a transvenous lead having electrodes intended for location in the right ventricular apex and in the superior vena cava. This electrode system is disclosed as useful for either ventricular or atrial defibrillation.

While systems employing epicardial patch electrodes are workable, a thoracotomy is required in order to apply the epicardial electrodes. It is generally believed that it would be desirable to produce an implantable defibrillation system that entirely avoids the necessity of a thoracotomy. To this end, there has been substantial work directed towards development of such systems, as disclosed in Kallok U.S. Pat. No. 4,727,877, Tacker, et al, U.S. Pat. No. 4,708,145, and U.S. Pat. No. 5,014,696 by Mehra, for an "Endocardial Defibrillation Electrode System". Other types of endocardial defibrillation electrodes are disclosed in Gold et al U.S. Pat. No. 4,481,953, Kinney, et al U.S. Pat. No. 4,161,952, Kiekhafer et al U.S. Pat. No. 4,934,049, and in U.S. Pat. No. 5,042,143 by Holleman, et al, for an "Method for Fabrication of Implantable Electrode". The Kinney, Gold, Kiekhafer, and Holleman patents all disclose endocardial defibrillation leads employing defibrillation electrodes fabricated from elongated coils of biocompatible metal, mounted exposed to the exterior of the defibrillation lead, for placement in the right ventricle and other locations within the heart. The above-cited Mehra patent discloses a variety of endocardial defibrillation electrodes intended for use in the atrium, ventricle and coronary sinus, all of which employ electrodes in the form of elongated coils of conductive biocompatible metals.

Concurrent with the development of lead systems adapted to treat ventricular fibrillation, there has also been some work directed to the development of lead systems to treat atrial fibrillation. Synchronized cardioversion using two electrodes located on a lead located in the right atrium is disclosed in Charms U.S. Pat. No. 3,738,370. A later system is disclosed in Mirowski et al U.S. Pat. No. 3,952,750, employing one electrode in the atrium and presumably a second electrode at an unspecified location.

An electrode lead system specifically designed for atrial defibrillation is disclosed in the article "Elective Countershock in atrial Fibrillation With an Intracardiac Electrode—A Preliminary Report, by Jain, et al, published in the Journal of the Association of Physicians of India, Vol. 18, pp 821–824, 1970. The lead in the system was provided with a 10 mm silver electrode for location in the right atrium and was tested in conjunction with either a second electrode located in the right atrium or a second, cutaneous electrode located on the left side of the chest wall. A second electrode system specifically designed for use in atrial cardioversion is disclosed in the article "Safety and feasibility of transvenous cardioversion in atrial tachycardia", by Blanc et al, published in Cardiac Pacing, edited by Gomez, Futura Pub. Co., 1985, pp 1526–1529. This electrode system employed a single lead with electrodes located in the atrium and pulmonary artery.

Atrial defibrillators are also known in the art. Specifically U.S. Pat. No. 5,165,403 "Defibrillation lead system and method of use" to Mehra describes a method of cardioverting the atrium of a human heart that includes insertion of first and second elongated electrodes tranvenously into the heart and associated vessels. One electrode is preferably located in the coronary sinus and great vein of the heart. The other electrode is preferably located in the vicinity of the atrium of the heart, spaced from the electrode located in the coronary sinus. In response to detection of fibrillation or in response to manual triggering, a defibrillation pulse is applied between the first and second electrodes to effect atrial cardioversion. Additionally, U.S. Pat. No. 5,433,729 "Atrial defibrillator, lead systems, and method" to Adams describes an implantable atrial defibrillator providing a pulse of defibrillating electrical energy to the atria of the heart in synchronism with sensed R waves in response to non-coincident sensing of an R wave at first and second areas of the heart. The defibrillating pulse is provided after a predetermined number of consecutive R waves are non-coincidently sensed to assure reliable synchronization. The atrial fibrillation detector of the defibrillator is normally disabled and is activated when the sensed ventricular activity indicates a probability of atrial fibrillation to conserve a depletable power source. A plurality of lead systems are also described for use with the atrial defibrillator which reduce the quantity of electrical energy required to defibrillate the heart and ensure that the delivered atrial defibrillating electrical energy is substantially confined to the atria of the heart. The '403 and '729 are incorporated by reference herein in their entireties.

In many patients, upon successful termination of atrial fibrillation by cardioversion and/or defibrillation, the immediate or near immediate reoccurrence of atrial fibrillation is a known problem. For example, Tse, et. al. describes a difference in p-wave width after low energy shocks in some patients in "Reoccurrence of Atrial Fibrillation after Successful Cardioversion with Transvenous Atrial Defibrillation is Associated with Prolonged P Wave", European Journal of Cardiology, Pacing and Electrophysiology, Vol 6, No 1, Page 55, June 1996. The authors' hypothesis is that some patients have a propensity to have a temporary increase in dispersion of Intra-Atrial Conduction Delay (IACD) that is an indicator of re-initiation of atrial fibrillation.

Standard defibrillators as described above (Mehra '403 and Adams '729) would re-detect the re-initiated fibrillation and re-shock the patient. If multiple re-initiations occurred, this would cause multiple fibrillation detections and treatments causing shortened defibrillator life, patient discomfort, and reduced quality of life. What is needed is a defibrillator that initiates preventive therapy after a successful cardioversion/defibrillation shock to prevent reoccurrence or re-initiation of fibrillation upon successful termination of an arrhythmic episode.

SUMMARY OF THE INVENTION

The present invention is directed toward the provision of an entirely endocardial defibrillation lead system particularly optimized for use in defibrillation or cardioversion of the atrium. The system disclosed includes coronary sinus, right atrial, and right ventricular electrodes, and may be embodied with the electrodes located on the same or different lead bodies. Additionally, bi-atrial pacing is incorporated to prevent the reoccurrence or re-initiation of atrial fibrillation after a successful cardioversion or defibrillation therapy.

According to the present invention, an implantable medical device for delivering a first therapy in response to variations in heart rhythm detected by electrodes inserted within a patient includes an amplifier generating p-waves in response to a signal between the electrodes, and a pacer timing/control circuit. In response to the first therapy being successful, the pacer timing/control circuit detects variations in subsequently generated p-waves, so that a second therapy is delivered in response to the detected variations in subsequently generated p-waves. According to a preferred embodiment of the present invention, the pacer timing/control circuit determines, subsequent to delivery of the second therapy, whether a width of a subsequent p-wave from the amplifier is greater than a predetermined threshold width, and delivery of the second therapy is repeated in response to the width of the p-wave being greater than the predetermined threshold width. According to another embodiment of the present invention, the pacer timing/control circuit determines, subsequent to delivery of the second therapy, whether a width of a p-wave is greater than a predetermined threshold width, and delivery of the second therapy is repeated in response to the width of the p-wave being greater than the predetermined threshold width.

BRIEF DESCRIPTION OF THE DRAWINGS

The features of the present invention which are believed to be novel are set forth with particularity in the appended claims. The invention, together with further objects and advantages thereof, may best be understood by making reference to the following description, taken in conjunction with the accompanying drawings, in the several figures of which like reference numerals identify like elements, and wherein:

FIG. 4 is a flow diagram illustrating the manner in which the atrial defibrillator of FIG. 1 may be implemented in accordance with the present invention; a method and apparatus for determining the width of depolarization of the atrium and for providing pacing of the left atrium of the heart if they exceed a predetermined width;

FIG. 5 is an alternative flow diagram illustrating the manner in which the atrial defibrillator of FIG. 1 may be implemented in accordance with the present invention; a method and apparatus for determining the width of depolarization of the atrium and for providing pacing of the left atrium of the heart if they exceed a predetermined width.

DETAILED DESCRIPTION OF THE PREFERRED EMBODIMENTS

Figure 1:
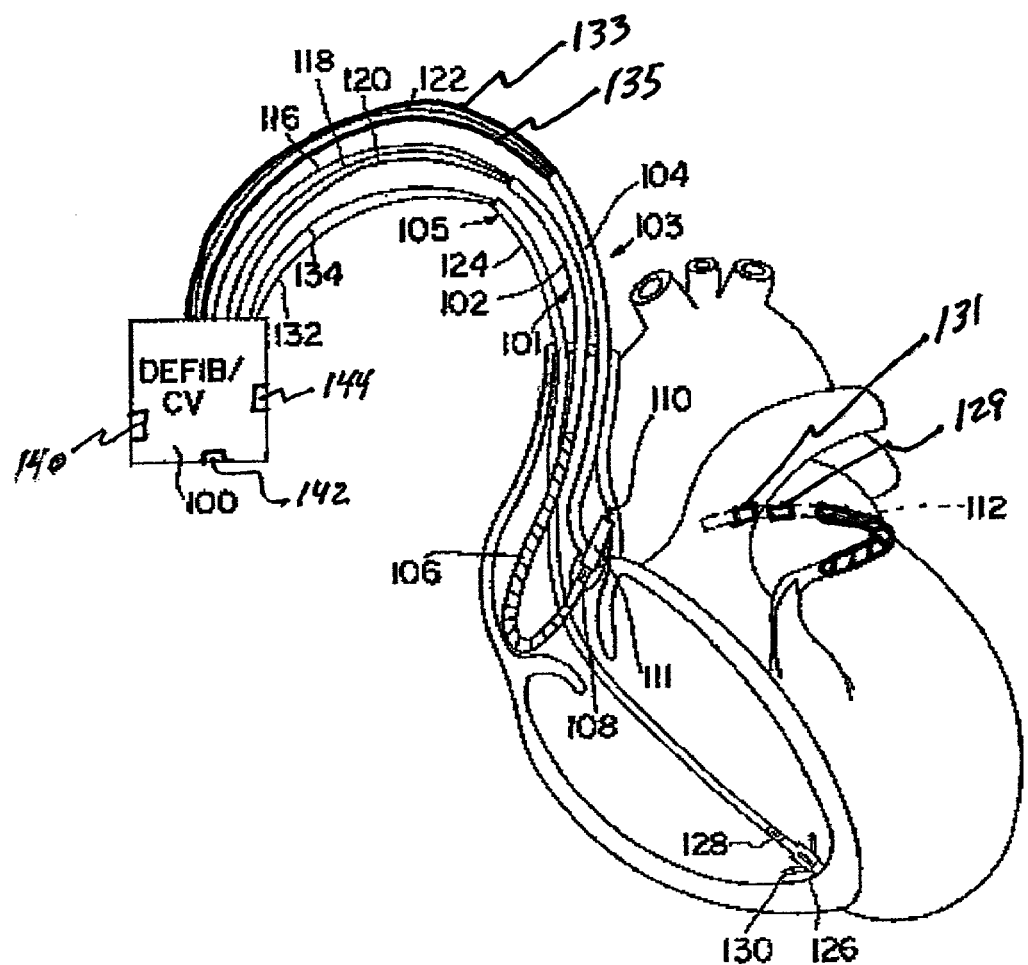
FIG. 1 illustrates a first embodiment of a cardioversion/defibrillation lead system according to the present invention employing a J-shaped atrial electrode located on a lead also provided with a pair of electrodes including a helical electrode for affixing the lead to the atrial wall and a separate lead carrying the coronary sinus electrode.

FIG. 1 is a cutaway view of the human heart in which a lead system suitable for use in practicing the present invention has been implanted. The lead system includes three leads. A right atrial lead 101 includes an elongated insulative lead body 102, to which a coiled defibrillation electrode 106 has been mounted. The distal end of the lead includes an electrode head 111, carrying a helical electrode 110 and a ring electrode 108. The electrodes 106, 108 and 110 are coupled to an implantable pacemaker/cardioverter/defibrillator 100 by means of conductors 116, 118 and 120. Electrodes 108 and 110 are employed for cardiac pacing and sensing in the atrium.

A coronary sinus lead 103 also has an elongated insulative lead body 104 which carries a coiled defibrillation electrode at its distal end, located as generally indicated at 112. Electrode 112 is located within the coronary sinus and the great cardiac vein. Preferably the proximal end of the electrode 112 is spaced about 3 to 8 cm from the opening of the coronary sinus into the right atrium. Electrode 112 is coupled to implantable pacemaker/cardioverter/defibrillator 100 by means of conductor 122. Additionally, ring electrodes 129 and 131 located proximally to electrode 112, are connected to pacemaker/cardioverter/defibrillator 100 via insulated conductors 133 and 135, are used for left atrial sensing and pacing.

A right ventricular pacing lead 105 also includes an elongated insulative lead body 124. The distal end of the lead 105 carries a tip electrode 126 and a ring electrode 128. The electrodes 126 and 128 are coupled to implantable pacemaker/cardioverter/defibrillator 100 by means of conductors 132 and 134. Electrodes 126 and 128 are used for cardiac pacing and sensing in the ventricle. Tines 130 anchor the distal end of the lead in the right ventricular apex. An additional electrode may be located on the housing of the device 100 and may be employed to accomplish pacing and sensing functions in conjunction with the other illustrated pacing and sensing electrodes. Although not illustrated, lead 124 may include an additional defibrillation electrode for location in the right ventricle. This ventricular defibrillation electrode may also be employed for atrial defibrillation. If the invention is embodied in a device capable of detecting ventricular tachyarrhythmias, such a ventricular defibrillation electrode would also be used for ventricular cardioversion and defibrillation.

Electrodes pairs 108/110, and 129/131 and, optionally, electrodes 126 and 128 are used by pacemaker/cardioverter/defibrillator 100 to sense the electrical activity of the atrium and optionally the ventricle to diagnose the presence of atrial tachycardias or fibrillation requiring delivery of high voltage cardioversion or defibrillation pulses, respectively. In response to the detection of tachycardia or fibrillation, pacemaker/cardioverter/defibrillator 100 generates a high voltage pulse between electrodes 106 and 112. Electrodes 108/110, 129/131 and 126/128, along with an electrode located on the housing of the device 100, may also be employed in order to deliver any of the various conventional pacing therapies, including pacing in single chamber (VVI, AII, etc.) modes or dual chamber (VDD, DVI, DDD, DDI, etc) modes.

Electrodes 140/142/144 are electrodes mounted on the case of pacemaker/cardioverter/defibrillator 100 to sense a subcutaneous ECG as substantially described in U.S. patent application Ser. No. 09/721,275 filed Nov. 22, 2000 "System and Method for Deriving a Virtual ECG or EGM Signal" incorporated herein by reference in its entirety. Additionally, the subcutaneous electrode array sensing of ECG is described in "Electrogram Signals Recorded from Acute and Chronic Pacemaker Implantation Sites in Pacemaker Patients", by Theres, et al, in PACE, Vol. 21, Jan. 1998, Part 1, pg 11–17.

In the embodiments disclosed in detail below, the pacemaker/cardioverter/defibrillator 100 operates in VVI pacing mode, using electrode 126 and an electrode mounted on the housing of the device for delivery of cardiac pacing pulses. Electrodes 128 and 126 are employed for sensing during VVI pacing. Electrode 128 and an electrode on the device housing may be employed for capture detection following delivery of overdrive pacing pulses during the synchronization sequence. The electrode on the housing may take the form of some or all of a conductive housing. Electrodes 108 and 110 are employed for atrial tachyarrhythmia detection and may be employed for atrial sensing and pacing if a dual chamber pacing mode is desired.

Figure 2:
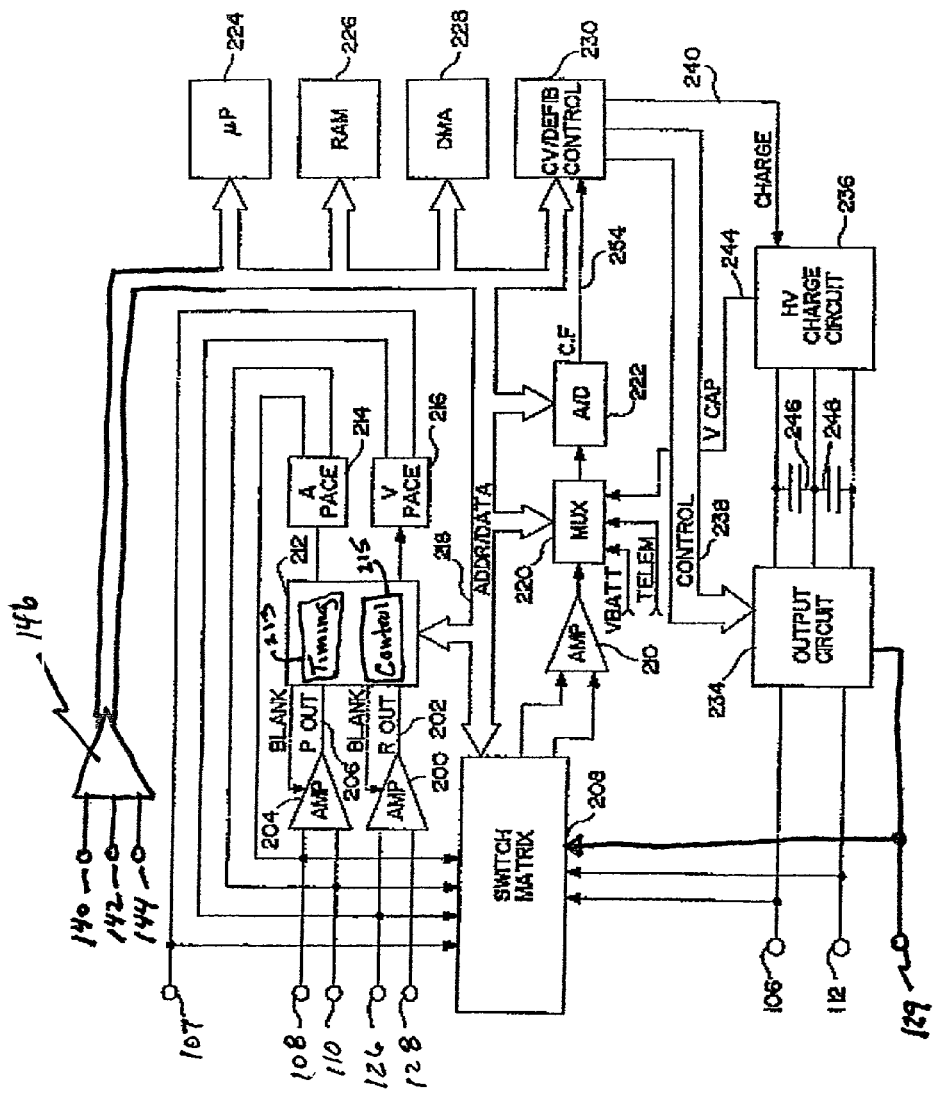
FIG. 2 is a schematic block diagram of a fully implantable atrial defibrillator embodying the present invention for applying defibrillating electrical energy to the atria of a human heart and which is shown in association with a human heart in need of atrial fibrillation monitoring and potential cardioversion of the atria.

FIG. 2 is a functional schematic diagram of an implantable pacemaker/cardioverter/defibrillator in which the present invention may usefully be practiced. This diagram should be taken as exemplary of the type of device in which the invention may be embodied, and not as limiting, as it is believed that the invention may usefully be practiced in a wide variety of device implementations, including cardioverter and defibrillators, which do not provide anti-tachycardia pacing therapies.

The device is provided with an electrode system including electrodes as illustrated in FIG. 1, with the addition of electrode 107, located on the housing of the implanted device. Electrode 112 is a defibrillation electrode located in the coronary sinus and great vein. Electrode 106 is a defibrillation electrode located in the right atrium and/or the superior vena cava. Both electrodes 112 and 106 are coupled to high voltage output circuit 234. Electrodes 128 and 126 are located on or in the right ventricle and are coupled to the R-wave amplifier 200, which preferably takes the form of an automatic gain controlled amplifier providing an adjustable sensing threshold as a function of the measured R-wave amplitude. A signal is generated on R-out line 202 whenever the signal sensed between electrodes 126 and 128 exceeds the present sensing threshold.

Electrodes 108 and 110 are located on or in the right atrium and are coupled to the P-wave amplifier 204, which preferably also takes the form of an automatic gain controlled amplifier providing an adjustable sensing threshold as a function of the measured P-wave amplitude. A signal is generated on P-out line 206 whenever the signal sensed between electrodes 108 and 110 exceeds the present sensing threshold. The general operation of the R-wave and P-wave amplifiers 200 and 204 may correspond to that disclosed in allowed, commonly assigned, co-pending U.S. Pat. No. 5,117,824, by Keimel, et al., for an Apparatus for Monitoring Electrical Physiologic Signals, incorporated herein by reference in its entirety.

An alternate embodiment incorporates subcutaneous electrode array electrodes 140/142/144 that are connected via ADDR/DATA bus 218 to amplifier 146 to increase the signal level for conversion via A/D converter 222 as substantially described in U.S. patent application Ser. No. 09/736,640 filed Dec. 14, 2000, "Atrial Aware VVI—A Method for Atrial Synchronous Ventricular (VDD/R) Pacing Using the Subcutaneous Electrode Array and a Standard Pacing Lead" incorporated herein by reference in its entirety. The p-wave width of the converted signal is measured via a PACER TIMING and CONTROL circuit 212, which includes various circuit elements, including timing circuitry 213 and control circuitry 215.

Switch matrix 208 is used to select which of the available electrodes are coupled to wide band (0.5–200 Hz) amplifier 210 for use in digital signal analysis. Selection of electrodes is controlled by the microprocessor 224 via data/address bus 218, which selections may be varied as desired. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal-processing methodologies known to the art. One representative example is U.S. Pat. No. 6,029,087 to Wohlgemuth, incorporated herein in its entirety by reference.

Switch matrix 208 is also used to select electrodes for use in performing the bi-atrial pacing function following delivery of cardioversion or defibrillation therapy pulses. Additionally, electrode 128 and electrode 107 located on the housing of the device may be so employed. Other electrode configurations are also easily selected. The signal from wide band amplifier 210, as digitized by A/D converter 222 may be stored and analyzed by microprocessor 224 during the delay period.

Bi-atrial pacing of the present invention may be as described in U.S. Pat. Nos. 6,070,101, 6,081,748 and 6,122,545, all to Struble, et al and U.S. Pat. No. 5,902,324 to Thompson, et al all incorporated by reference in their entireties. The Struble '101, '748 and '545 patents describe multi-chamber cardiac pacing systems for providing synchronous pacing to at least the two upper heart chambers or the two lower heart chambers or to three heart chambers or to all four heart chambers employing programmable conduction delay window (CDW) times timed out from paced and sensed events occurring in each heart chamber. The synchronous pacing of one of the right and left heart chambers is provided on demand following expiration of programmable pace and sense CDWs that are started by both a paced event and a sensed event first occurring in the other of the right and left heart chambers. The delivery of the pacing pulse is inhibited by a sensed event detected in the other of the right and left heart chambers before the expiration of the corresponding CDW. In a four channel atrial and ventricular pacing system, the right and left atrial chambers are sensed and paced as necessary upon at the end of a V-A escape interval and right and left AV delays are commenced for sensing ventricular depolarizations in the right and left ventricles. The four channel system is programmable to pace and sense in three selected heart chambers.

The Thompson '324 patent describes a multi-chamber cardiac pacing system for providing synchronous pacing to at least the two upper heart chambers or the two lower heart chambers or to three heart chambers or to all four heart chambers employing one or more field density clamp (FDC) sense amplifiers for accurately sensing and timing cardiac depolarizations of the right and left heart chambers.

The remainder of the circuitry of FIG. 2 is dedicated to the provision of cardiac pacing, cardioversion and defibrillation therapies, and, for purposes of the present invention may correspond to circuitry known in the prior art. The pacer timing/control circuitry 212 includes programmable digital counters which control the basic time intervals associated with DDD, VVI, DVI, VDD, AAI, DDI and other modes of single and dual chamber pacing well known to the art. Circuitry 212 also controls escape intervals associated with anti-tachyarrhythmia pacing in both the atrium and the ventricle, employing any anti-tachyarrhythmia pacing therapies known to the art.

Intervals defined by pacing circuitry 212 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 224, in response to stored data in memory 226 and are communicated to the pacing circuitry 212 via address/data bus 218. Pacer circuitry 212 also determines the amplitude of the cardiac pacing pulses under control of microprocessor 224.

During pacing, the escape interval counters within pacer timing/control circuitry 212 are reset upon sensing of R-waves and P-waves as indicated by a signals on lines 202 and 206, and in accordance with the selected mode of pacing on timeout trigger generation of pacing pulses by pacer output circuitry 214 and 216, which are coupled to electrodes 126 and 107, for ventricular pacing and to electrodes 108 and 110 for atrial pacing. The escape interval counters are also reset on generation of pacing pulses, and thereby control the basic timing of cardiac pacing functions, including anti-tachyarrhythmia pacing. The durations of the intervals defined by the escape interval timers are determined by microprocessor 224, via data/address bus 218. The value of the count present in the escape interval counters when reset by sensed R-waves and P-waves may be used to measure the durations of R-R intervals, P-P intervals, P-R intervals and R-P intervals, which measurements are stored in memory 226 and used to detect the presence of tachyarrhythmias.

Microprocessor 224 operates as an interrupt driven device, and is awakened by interrupts from pacer timing/control circuitry 212 corresponding to the occurrence sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts.

For example, using pacer timing/control circuitry 212, R-wave amplifier 206, electrodes 107, 126 and 128, and pacer output circuitry 216, a pace or a sense interrupt is generated in response to a sensed or paced ventricular depolarization or R-wave, the intervals separating that R-wave from the immediately preceding R-wave, paced or sensed (R-R interval) and the interval separating the paced or sensed R-wave from the preceding atrial depolarization, paced or sensed (P-R interval), all of which may be stored. Similarly, using pacer timing/control circuitry 212, P-wave amplifier 204, electrodes 208 and 110, and pacer output circuitry 214, a pace or sense interrupt is generated in response to the occurrence of a sensed or paced atrial depolarization (P-wave), the intervals separating the sensed P-wave from the immediately preceding paced of sensed atrial contraction (P-P Interval) and the interval separating the sensed P-wave from the immediately preceding sensed or paced ventricular depolarization (R-P interval) may be stored. Preferably, a portion of the memory 226 is configured as a plurality of recirculating buffers, capable of holding a preceding series of measured intervals, which may be analyzed in response to the occurrence of a pace or sense interrupt to determine whether the patient's heart is presently exhibiting an atrial tachyarrhythmia.

Detection of atrial tachyarrhythmias, as employed in the present invention, may correspond to tachyarrhythmia detection algorithms known to the art. For example, presence of atrial tachyarrhythmia may be confirmed by means of detection of a sustained series of short P-P intervals of an average rate indicative of tachyarrhythmia or an unbroken series of short P-P intervals. The suddenness of onset of the detected high rates, the stability of the high rates, or a number of other factors known to the art may also be measured at this time. Appropriate detection methodologies measuring such factors are described in U.S. Pat. No. 4,726,380, issued to Vollmann, U.S. Pat. No. 4,880,005, issued to Pless et al and U.S. Pat. No. 4,830,006, issued to Haluska et al. Alternatively, the tachyarrhythmia analysis and recognition methodology disclosed in the article "Automatic Tachycardia Recognition" by Arzbaecher et al., published in Pace, May-June, 1984, pp. 541–547. However, one of the advantages of the present invention is that it is believed practicable in conjunction with all prior art atrial tachycardia detection algorithms.

The device also detects termination of atrial tachyarrhythmias, for example by detection of a sequence sequential P-P intervals greater than a preset duration, or by detection of a average atrial rate, over a series of p-waves, which is less than a preset value. Detection of termination is preferably operative during charging of the high voltage output capacitors 246 and 248, as well as during the cardioversion or defibrillation synchronization sequence according to the present invention.

In the event that an atrial tachyarrhythmia is detected, and an anti-tachyarrhythmia pacing regimen is desired, appropriate timing intervals for controlling generation of anti-tachyarrhythmia pacing therapies are loaded from microprocessor 224 into the pacer timing and control circuitry 212, to control the operation of the escape interval counters therein and to define refractory periods during which detection of R-waves and P-waves is ineffective to restart the escape interval counters.

Alternatively, circuitry for controlling the timing and generation of antitachycardia pacing pulses as described in U.S. Pat. No. 4,577,633, issued to Berkovits et al on Mar. 25, 1986, U.S. Pat. No. 4,880,005, issued to Pless et al on Nov. 14, 1989, U.S. Pat. No. 7,726,380, issued to Vollmann et al on Feb. 23, 1988 and U.S. Pat. No. 4,587,970, issued to Holley et al on May 13, 1986, all of which are incorporated herein by reference in their entireties may also be used.

In the event that generation of a cardioversion or defibrillation pulse is required, microprocessor 224 employs the counters in circuitry 212 to control timing of such cardioversion and defibrillation pulses, as well as associated refractory periods. In response to the detection of an atrial tachyarrhythmia requiring a cardioversion or defibrillation pulse, microprocessor 224 activates cardioversion/defibrillation control circuitry 230, which initiates charging of the high voltage capacitors 246 and 248 via charging circuit 236, under control of high voltage charging control line 240. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212.

Following delivery of the fibrillation or tachycardia therapy the microprocessor then returns the device to pacing and awaits the next successive interrupt due to pacing or the occurrence of a sensed atrial or ventricular depolarization.

Figure 3A:
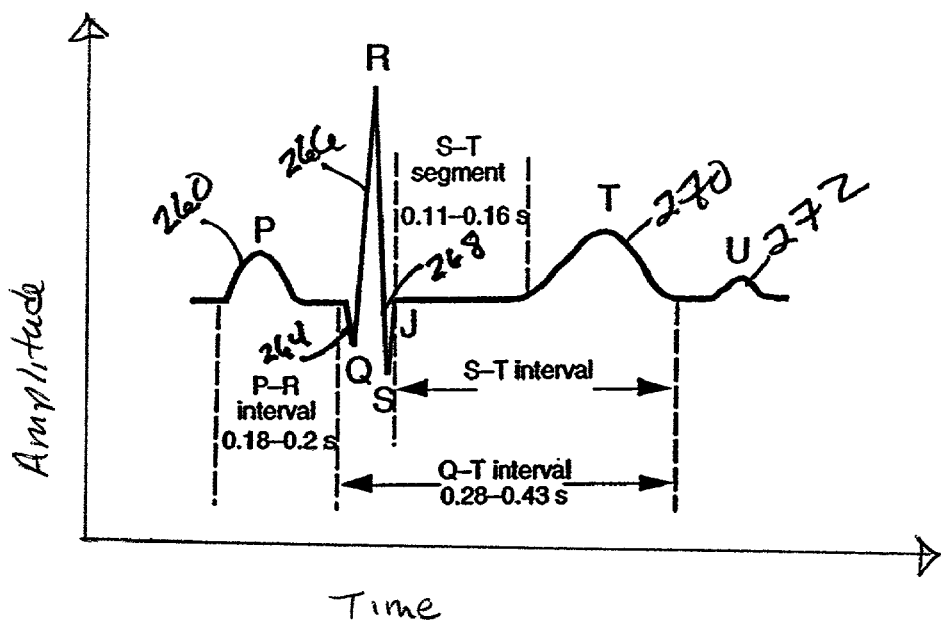
FIG. 3A is a graphical representation of a normal sinus rhythm as depicted on an electrocardiogram (ECG)

FIG. 3A is a graphical representation of a normal sinus rhythm as depicted on an electrocardiogram (ECG). As illustrated in FIG. 3A, a normal cardiac cycle is a repetitive waveform characterized by a periodic PQRST electrical activation sequence of the upper and lower heart chambers. The PQRST sequence is associated with the sequential depolarization and contraction of the atria followed by the depolarization and contraction of the ventricles, and successive PQRST complexes are separated by a baseline or isoelectric region. The PQRST electrical activation sequence commences with a P-wave 260 indicative of the depolarization and contraction of the atria. In a normal sinus rhythm, P-wave 260 has a rounded shape which does not include notches or peaks and is typically less than or equal to 80 msec in width. P-wave 260 is followed by a QRS complex, indicative of the depolarization and contraction of the ventricles, and which includes a Q-wave 264, an R-wave 266 and an S-wave 268. Q-wave 264 and S-wave 268 represent negative (downward) deflections, while R-wave 266 represents positive (upward) deflections. Finally, QRS complex 262 is followed by a rounded asymmetrically shaped T-wave 270, which results from ventricular repolarization, and a U-wave 272, which follows and has the same polarity as T-wave 270 and tends to become more evident with hypokalemia, bradycardia, and age.

Figure 3B:
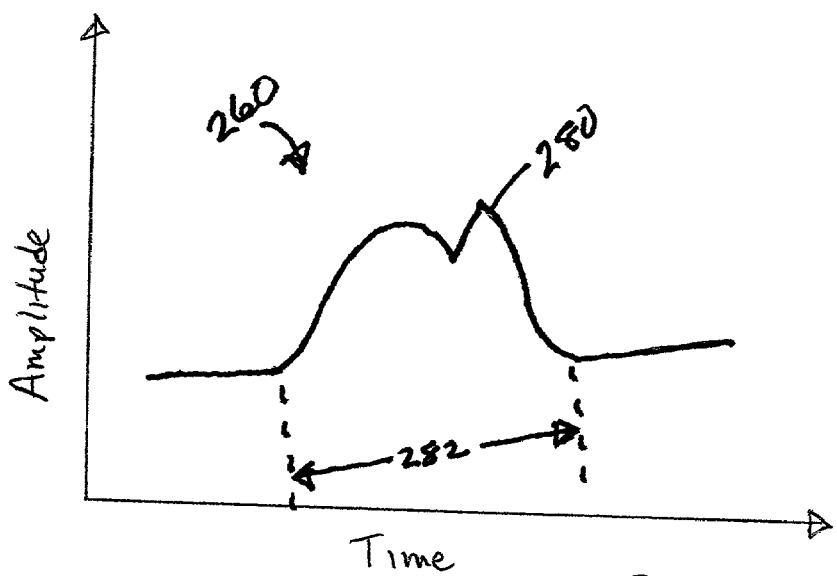
FIG. 3B is a graphical representation of the effects of conduction delay on a P-wave of a waveform representation of a cardiac cycle.

FIG. 3B is a graphical representation of the effects of conduction delay on a P-wave of a waveform representation of a cardiac cycle. As illustrated in FIG. 3B, when dispersion of intra-atrial conduction delay increases, notches 280 tend to be formed on P-wave 260, and a width 282 of P-wave 260 tends to increase. The present invention utilizes these tendencies in the morphology of P-wave 260 resulting from increased conduction delay, indicating potential spontaneous re-initiation of atrial fibrillation, to temporarily initiate bi-atrial pacing to prevent the immediate or near immediate reoccurrence of atrial fibrillation subsequent to a successful termination of atrial fibrillation by cardioversion and/or defibrillation, as will be described below.

FIG. 4 is a functional flowchart illustrating the overall operation of the device according to the present invention. The flowchart begins at step 302. Sense amp 204 senses p-waves at step 304, and using the sensed p-waves from p-wave amplifier 204, pacer timing/control circuitry 212 detects the presence of atrial tachyarrhythmia at step 306 by sensing a sustained series of short intervals between the sensed p-waves, i.e., sustained short P-P intervals, less than an average rate. For example, pacer timing/control circuit 212 detects that atrial tachyarrhythmia is present when sustained short P-P intervals less than 500 msec. are sensed, or when an unbroken series of short P-P intervals is detected. In addition, the suddenness of onset of the detected high rates, the stability of the high rates, or a number of other factors known to the art may also be measured by pacer timing/control circuit 212.

If an arrhythmia is detected, therapy is provided at step 308 via output circuit 234, HV charge circuit 236, and CV/defib control 230. If no arrhythmia is detected, pacer timing/control circuitry 212 continues to monitor intrinsic p-waves from p-wave amplifier 204. If a therapy is delivered at step 308, a determination is made by pacer timing/control circuitry 212 of the success of the therapy delivered at step 310, for example, by detecting a sequence of sequential P-P intervals from p-wave amplifier 204 greater than a preset duration, or by detection of an average atrial rate, over a series of the received p-waves, which is less than a preset value. It is understood that according to the present invention, any method may be used for detecting the presence of atrial tachyarrthythmia and for detecting the success of a delivered therapy in steps 306 and 308, respectively.

If not successful, the therapy is retried or increased to a higher level as is well known in the art. If the therapy is successful, pacer timing/control circuit 212 continues to sense p-waves from amplifier 204 at step 312. Pacer timing/control circuit 212 then determines, using the methods for detecting the presence of atrial tachyarrhythmia described in step 306, whether atrial tachyarrhythmia is detected in step 313. If an arrhythmia is detected in step 313, the process returns to step 308 and a therapy is provided. If an arrhythmia is not detected in step 313, the intrinsic p-wave widths of the p-waves from amplifier 204 are compared to a preset, or pre-programmed threshold width by pacer timing and control circuit 212 at step 314. This threshold width may be a preset or programmed msec. value (e.g., 10–50 msec) over the normal intrinsic width of a p-wave, i.e., 80 msec., or, alternatively, may be of a proportionately greater measure over a preset width of a p-wave, such as a preset or programmed percent (e.g., 5–20%) increase over the normal intrinsic width of a p-wave. If the measured p-wave widths do not exceed the threshold width, the process is completed at step 320. However, if at step 314, the threshold width is exceeded, bi-atrial pacing begins via A pace 214 and switch matrix 208 at a preset or pre-programmed delay at step 316. Bi-atrial pacing continues for a preset, programmed time (e.g., for 1–5 minutes) via timer 212 at step 318 with the process again completing at step 320.

Turning now to FIG. 5, an alternative embodiment of the functional flowchart of FIG. 4 is shown. The flowchart begins at step 402. Sense amp 204 senses p-waves at step 404, and using the sensed p-waves from p-wave amplifier 204, pacer timing/control circuitry 212 detects the presence of atrial tachyarrhythmia at step 406 by sensing a sustained series of short intervals between the sensed p-waves, i.e., sustained short P-P intervals less than an average rate. For example, pacer timing/control circuit 212 detects that atrial tachyarrhythmia is present when sustained short P-P intervals less than 500 msec. are detected, or when an unbroken series of short P-P intervals is detected. In addition, the suddenness of onset of the detected high rates, the stability of the high rates, or a number of other factors known to the art may also be measured and utilized to detect the presence of atrial tachyarrhythmia in step 406.

If an arrhythmia is detected by pacer timing/control circuitry 212 at step 406, therapy is provided at step 408 via output circuit 234, RV charge circuit 236, and CV/defib control 230. If no arrhythmia is detected, pacer timing/control circuitry 212 continues to monitor intrinsic p-waves from p-wave amplifier 204. If a therapy is delivered at step 408, a determination of the success of the therapy is made by pacer timing/control circuitry 212 at step 410 by detecting a sequence of sequential P-P intervals from p-wave amplifier 204 greater than a preset duration, for example, or by detection of an average atrial rate over a series of the received p-waves which is less than a preset value. It is understood that, according to the present invention, any method may be used for detecting the presence atrial tachyarrhythmia and for detecting the success of a delivered therapy in steps 406 and 410, respectively.

If pacer timing/control circuitry 212 determines in step 410 that the therapy is not successful, the therapy is retried or increased to a higher level as is well known in the art. If the therapy is successful, pacer timing/control circuit 212 continues to monitor p-waves from amplifier 204 at step 412. Pacer timing/control circuit 212 then determines, using the methods for detecting the presence of atrial tachyarrhythmia described in step 406, whether atrial tachyarrhythmia is detected in step 413. If an arrhythmia is detected in step 413, the process returns to step 408 and a therapy is provided. If an arrhythmia is not detected in step 413, the intrinsic p-wave widths of the p-waves from amplifier 204 are compared to a preset or pre-programmed threshold width by pacer timing and control circuit 212 at step 414. If the intrinsic p-wave widths do not exceed the threshold, the process is completed at step 420. However, if at step 414, the threshold width is exceeded, bi-atrial pacing begins via A pace 214 and switch matrix 208 at a pre-programmed delay at step 416. According to the present invention, bi-atrial pacing continues for a preset time (e.g., 1–5 minutes) by timing circuitry 213 of pacer timing/control circuit 212 whereby the p-wave width is measured and again compared to the preset or pre-programmed threshold width at step 418. This threshold width may be a preset or programmed msec value (e.g., 10–50 msec) over the normal intrinsic width of a p-wave, i.e., 80 msec., or, alternatively, may be of a proportionately greater measure over a normal width of a p-wave, such as a preset or programmed percent (e.g., 5–20%) increase over the normal intrinsic width of a p-wave. Once the measured p-wave width is determined to be below the threshold width, the process terminates at step 420. If, on the other hand, the measured p-wave width is determined to be greater than the preset or pre-programmed width threshold width in step 418, timing circuit 213 of pacer timing control circuit 212 is reset and bi-atrial pacing continues at step 416.In this way, according to the present invention, once bi-atrial pacing is initially delivered for the preset time period, if the width of the p-wave continues to be greater than the threshold width, indicating a continued propensity for re-initiation of atrial fibrillation, delivery of bi-atrial pacing is repeated for the preset time period. As a result, the bi-atrial pacing is continued until this propensity for re-initiation is reduced.

It is understood that, while the present invention has been described using electrodes 108 and 110, place on or within the right atrium and connected to p-wave amplifier 204, to generate p-waves, the present invention is not limited use of electrodes 108 and 110 placed on within the right atrium. Rather, it is envisioned that the present invention could utilize other methods for sensing, recording and acquiring electrocardiographic data (ECG) and tracings from an implanted medical device. For example, the present invention can be utilized using subcutaneous electrode array electrodes 140, 142 and 144, with pacer timing/control circuit 212 comparing p-waves received from electrodes 140, 142 and 144 and comparing the p-waves to the threshold to determine whether to initiate bi-atrial pacing subsequent to a successfully delivered therapy, as described above.

A method of collecting ECG tracings from a set of subcutaneous electrodes, or a subcutaneous electrode array (SEA), has been described in U.S. Pat. No. 5,331,966 to Bennett, incorporated herein by reference, which discloses a method and apparatus for providing an enhanced capability of detecting and gathering electrical cardiac signals via an array of relatively closely spaced subcutaneous electrodes (located on the body of an implanted device). More recently, a patent application entitled "*Surround Shroud Connector and Electrode Housings for a Subcutaneous Electrode Array and Leadless ECGs*", by Ceballos, et al., filed on Oct. 26, 2000, Ser. No. 09/697,438, incorporated herein by reference in its totality, discloses an alternate method and apparatus for detecting electrical cardiac signals via an array of subcutaneous electrodes located on a shroud circumferentially placed on the perimeter of an implanted pacemaker. Similarly, a patent application entitled "*Subcutaneous Electrode for Sensing Electrical Signals of the Heart*", by Brabec et al, filed Oct. 31, 2000, Ser. No. 09/703,152, incorporated herein by reference in its totality, discloses the use of a spiral electrode using in conjunction with the shroud described in the Ceballos et al disclosure. In addition, two applications, entitled "*Multilayer Ceramic Electrodes for Sensing Cardiac Depolarization Signals*", by Guck et al, filed Oct. 25, 2000, Ser. No. 09/696,365 and "*Thin Film electrodes for Sensing Cardiac Depolarization Signals*" by Guck and Donders, filed Dec. 13, 2000, Ser. No. 09/736,046, both incorporated herein by reference in their totality, disclosed the use of sensing electrodes placed into recesses incorporated along and into the peripheral edge of the implantable pacemaker. Finally, the submission entitled, "*Subcutaneous Electrode Array Virtual ECG Lead*" by Panken and Reinke, filed Nov. 22, 2000, Ser. No. 09/721,275, also incorporated by reference to its entirety, describes the algorithm used by the implanted device that compiles the ECG from any two subcutaneous electrodes found in the SEA. The preceding specific embodiments are illustrative of the practice of the invention. It is to be understood, therefore, that other expedients known to those of skill in the art or disclosed herein may be employed. In the following claims, means-plus-function clauses are intended to cover the structures described herein as performing the recited function and not only structural equivalents but also equivalent structures. For example, although a nail and a screw may not be structural equivalents in that a nail employs a cylindrical surface to secure wooden parts together, whereas a screw employs a helical surface, in the environment of fastening wooden parts, a nail and a screw are equivalent structures. It is therefore to be understood, that within the scope of the appended claims, the invention may be practiced otherwise than as specifically described without actually departing from the spirit and scope of the present invention.

What is claimed is:

1. A method for implementing atrial defibrillation, comprising the steps of:
   delivering a first therapy in response to detection of an atrial tachyarrhythmia of a patient;
   determining whether the first therapy was successful;
   determining, following a determination that the first therapy was successful, variations in morphology of a subsequent waveform representation of a cardiac cycle of the patient; and
   delivering a second therapy in response to both determining the first therapy was successful and the determined variations.

2. The method of claim 1, wherein the step of determining variations determines whether a width of a p-wave is greater than a predetermined threshold width.

3. The method of claim 2 wherein the predetermined threshold width is greater than a normal intrinsic width of a p-wave.

4. The method of claim 3, wherein the predetermined threshold width is between approximately 10 and 50 msec greater than the normal intrinsic width of a p-wave.

5. The method of claim 2, wherein the predetermined threshold width is of a proportionately greater measure over a normal width of a p-wave.

6. The method of claim 5, wherein the proportionately greater measure includes a percent increase between approximately 5 and 20 percent.

7. The method of claim 1, wherein the second therapy is delivered for a predetermined time period.

8. The method of claim 7, wherein the predetermined time period is between approximately 1 and 5 minutes.

9. The method of claim 1, wherein the step of determining variations further comprises determining, after delivery of the second therapy, whether a width of a subsequent p-wave is greater than a predetermined threshold width.

10. The method of claim 9, wherein delivery of the second therapy is repeated in response to the width of the subsequent p-wave being greater than the predetermined threshold width.

11. The method of claim 1, further comprising the step of amplifying a signal between electrodes for generating the subsequent waveform representation.

12. The method of claim 11, wherein the electrodes comprise subcutaneous electrode array electrodes.

13. An implantable medical device, comprising:
means for delivering a first therapy in response to detection of an atrial tachyarrhythmia;
means for determining whether the first therapy was successful;
an amplifier sensing p-waves between electrodes and providing an output signal representative of the morphology of a sensed p-wave;
a pacer timing/control circuit receiving the amplifier output signal and, following a determination that the first therapy was successful, delivering a second therapy in response to both determining the first therapy was successful and detection of variations in morphology of subsequent sensed p-waves.

14. The device of claim 13, wherein the pacer timing/control circuit determines whether a width of a p-wave is greater than a predetermined threshold width.

15. The device of claim 14 wherein the predetermined threshold width is greater than a normal intrinsic width of a p-wave.

16. The device of claim 15, wherein the predetermined threshold width is between approximately 10 and 50 msec greater than the normal intrinsic width of a p-wave.

17. The device of claim 14, wherein the predetermined threshold width is a proportionately greater measure over a normal width of a p-wave.

18. The device of claim 17, wherein the proportionately greater measure includes a percent increase between approximately 5 and 20 percent.

19. The device of claim 13, wherein the pacer timing/control circuit determines, subsequent to delivery of the second therapy, whether a width of a subsequent p-wave is greater than a predetermined threshold width.

20. The device of claim 19, wherein delivery of the second therapy is repeated in response to the width of the subsequent p-wave being greater than the predetermined threshold width.

21. The device of claim 13, wherein the first therapy is a defibrillation pulse and the second therapy is bi-atrial pacing.

22. The device of claim 13, wherein the electrodes comprise subcutaneous electrode array electrodes.

23. An implantable medical device, comprising:
means for delivering a first therapy in response to detection of an atrial tachyarrhythmia of a patient;
means for determining whether the first therapy was successful;
means for determining, following a determination that the first therapy was successful, variations in morphology of a subsequent waveform representation of a cardiac cycle of the patient; and
means for delivering a second therapy in response to both the atrial tachyarrhythmia not being detected subsequent to the delivered first therapy and the determined variations.

24. The device of claim 23, wherein the means for determining variations determines whether a width of a p-wave is greater than a predetermined threshold width.

25. The device of claim 24 wherein the predetermined threshold width is greater than a normal intrinsic width of a p-wave.

26. The device of claim 25, wherein the predetermined threshold width is between approximately 10 and 50 msec greater than the normal intrinsic width of a p-wave.

27. The device of claim 24, wherein the predetermined threshold width is of a proportionately greater measure over a normal width of a p-wave.

28. The device of claim 27, wherein the proportionately greater measure includes a percent increase between approximately 5 and 20 percent.

29. The device of claim 23, wherein the means for delivering a second therapy delivers the second therapy for a predetermined time period.

30. The device of claim 29, wherein the predetermined time period is between approximately 1 and 5 minutes.

31. The device of claim 23, wherein the means for determining variations determines, after delivery of the second therapy, whether a width of a subsequent p-wave is greater than a predetermined threshold width.

32. The device of claim 31, wherein the means for delivering a second therapy repeats delivery of the second therapy in response to the width of the subsequent p-wave being greater than the predetermined threshold width.

33. The device of claim 23, further comprising means for amplifying a signal between electrodes for generating the subsequent waveform representation.

34. The device of claim 33, wherein the electrodes comprise subcutaneous electrode array electrodes.

35. The device of claim 23, wherein the first therapy is a defibrillation pulse and the second therapy is bi-atrial pacing.

* * * * *